United States Patent
Albashir et al.

(10) Patent No.: US 12,121,555 B1
(45) Date of Patent: Oct. 22, 2024

(54) **METHOD FOR INHIBITING ENZYME ACTIVITY USING *BOSCIA SENEGALENSIS***

(71) Applicant: KING FAISAL UNIVERSITY, Al-Ahsa (SA)

(72) Inventors: Abdalla Ahmed Albashir, Al-Ahsa (SA); Khansa Alshambatya, Sennar (SD); Sakina Yagia, Khartoum (SD); Amel Yousef Ebrahim, Al-Ahsa (SA)

(73) Assignee: KING FAISAL UNIVERSITY, Al-Ahsa (SA)

( * ) Notice: Subject to any disclaimer, the term of this patent is extended or adjusted under 35 U.S.C. 154(b) by 0 days.

(21) Appl. No.: 18/643,408

(22) Filed: Apr. 23, 2024

Related U.S. Application Data

(63) Continuation of application No. 18/402,675, filed on Jan. 2, 2024, now abandoned.

(51) Int. Cl.
*A61K 36/18* (2006.01)
*C12N 9/99* (2006.01)

(52) U.S. Cl.
CPC ............... *A61K 36/18* (2013.01); *C12N 9/99* (2013.01); *A61K 2236/15* (2013.01); *A61K 2236/17* (2013.01); *A61K 2236/333* (2013.01); *A61K 2236/35* (2013.01); *A61K 2236/53* (2013.01)

(58) Field of Classification Search
None
See application file for complete search history.

(56) References Cited

FOREIGN PATENT DOCUMENTS

KR 100255278 B1 5/2000

OTHER PUBLICATIONS

Dicko (Applied Biochemistry and Biotechnology (2001), vol. 94, pp. 225-241).*
Mary Gulumian et al; "African Herbal Remedies with Antioxidant Activity: A Potential Resource Base for Wound Treatment"; Evid Based Complement Alternat Med. 2018; 2018: 4089541. Published online Nov. 22, 2018. doi: 10.1155/2018/4089541.
Mamoudou H. Dicko et al; "Polysaccharide hydrolases from leaves of Boscia senegalensis; Properties of endo-(1-→3)-β-D-glucanase"; Applied Biochemistry and Biotechnology vol. 94, pp. 225-241 (2001).
Ronald Romuald Bebey Ngom Vougat et al; "Antioxidant activity and phytochemical constituent of two plants used to manage foot and mouth disease in the Far North Region of Cameroon"; J Intercult Ethnopharmacol. Jan.-Mar. 2015; 4(1): 40-46. Published online Nov. 28, 2014. doi: 10.5455/jice.20141020064838.
Alfred Maroyi; "Review of medicinal uses, phytochemistry and pharmacological properties of Boscia senegalensis"; Alfred Maroyi /J. Pharm. Sci. & Res. vol. 11(9), 2019, 3355-3361.
Abubaker M. A. Morgan et al; "A New Flavonol Glycoside from the Leaves of Boscia senegalensis"; Bull. Korean Chem. Soc. 2014, vol. 35, No. 12 3447 http://dx.doi.org/10.5012/bkcs.2014.35.12.3447.
Mahamane Idi Issa Abdoulahi et al, "Ethno Botanical, Pharmacology and Phytochemistry of widely used medicinal plants in Niger: A Review"; Journal of Medicinal Plants Studies 2022; 10(4): 46-60.
Aïssatou Alioune Gaye et al; "Using Boscia senegalensis leaves and fruits as a source of polyphenol, and micronutrients to improve antioxidant activity"; IOSR Journal of Applied Chemistry (IOSR-JAC) e-ISSN: 2278-5736. vol. 15, Issue 6 Ser. I (Jun. 2022), pp. 09-16 www.iosrjournals.org.

* cited by examiner

*Primary Examiner* — Susan Hoffman
(74) *Attorney, Agent, or Firm* — Nath, Goldberg & Meyer; Joshua B. Goldberg

(57) ABSTRACT

A method of inhibiting enzyme activity using an extract of *Boscia senegalensis*. In an embodiment, the extract is obtained from leaves of *Boscia senegalensis*. In an embodiment, the enzyme is one or more selected from the group consisting of acetylcholinesterase, butyrylcholinesterase, tyrosinase, α-amylase, and glucosidase.

5 Claims, No Drawings

METHOD FOR INHIBITING ENZYME ACTIVITY USING *BOSCIA SENEGALENSIS*

CROSS-REFERENCE TO RELATED APPLICATION

This application is a continuation of U.S. patent application Ser. No. 18/402,675, filed on Jan. 2, 2024, now abandoned the entire contents of which are incorporated herein by reference.

BACKGROUND

1. Field

The present disclosure relates to inhibiting enzyme activity and, particularly, to a method of inhibiting enzyme activity using *Boscia senegalensis*.

2. Description of the Related Art

Specific enzyme inhibitors find a wide range of applications in the medical, pharmaceutical, biotechnology, and food and agriculture industries. Inhibitors of a-glucosidase and $\alpha$-Amylase, for example, are increasingly finding therapeutic applications in metabolic disorders such as diabetes mellitus and obesity. Tyrosinase inhibitors are useful in minimizing melanin production. Acetylcholinesterase and butyrylcholinesterase inhibitors are useful for treating neurodegenerative diseases and conditions, including Alzheimer's disease.

Enzymatic inhibitors derived from natural sources are ideal for treating many diseases primarily because they are better tolerated by the human body.

Thus, a method for inhibiting enzyme activity solving the aforementioned problems is desired.

SUMMARY

In an embodiment, the present subject matter relates to a method of inhibiting enzyme activity using an extract of *Boscia senegalensis*. In an embodiment, the extract is obtained from leaves of *Boscia senegalensis*. In an embodiment, the enzyme is selected from the group consisting of acetylcholinesterase, butyrylcholinesterase, tyrosinase, $\alpha$-amylase, and glucosidase.

These and other features of the present subject matter will become readily apparent upon further review of the following specification.

DETAILED DESCRIPTION OF THE PREFERRED EMBODIMENTS

The following definitions are provided for the purpose of understanding the present subject matter and for construing the appended patent claims.

Definitions

Throughout the application, where compositions are described as having, including, or comprising specific components, or where processes are described as having, including, or comprising specific process steps, it is contemplated that compositions of the present teachings can also consist essentially of, or consist of, the recited components, and that the processes of the present teachings can also consist essentially of, or consist of, the recited process steps.

It is noted that, as used in this specification and the appended claims, the singular forms "a", "an", and "the" include plural references unless the context clearly dictates otherwise.

In the application, where an element or component is said to be included in and/or selected from a list of recited elements or components, it should be understood that the element or component can be any one of the recited elements or components, or the element or component can be selected from a group consisting of two or more of the recited elements or components. Further, it should be understood that elements and/or features of a composition or a method described herein can be combined in a variety of ways without departing from the spirit and scope of the present teachings, whether explicit or implicit herein.

The use of the terms "include," "includes", "including," "have," "has," or "having" should be generally understood as open-ended and non-limiting unless specifically stated otherwise.

The use of the singular herein includes the plural (and vice versa) unless specifically stated otherwise. In addition, where the use of the term "about" is before a quantitative value, the present teachings also include the specific quantitative value itself, unless specifically stated otherwise. As used herein, the term "about" refers to a ±10% variation from the nominal value unless otherwise indicated or inferred.

Unless defined otherwise, all technical and scientific terms used herein have the same meaning as commonly understood to one of ordinary skill in the art to which the presently described subject matter pertains.

Where a range of values is provided, for example, concentration ranges, percentage ranges, or ratio ranges, it is understood that each intervening value, to the tenth of the unit of the lower limit, unless the context clearly dictates otherwise, between the upper and lower limit of that range and any other stated or intervening value in that stated range, is encompassed within the described subject matter. The upper and lower limits of these smaller ranges may independently be included in the smaller ranges, and such embodiments are also encompassed within the described subject matter, subject to any specifically excluded limit in the stated range. Where the stated range includes one or both of the limits, ranges excluding either or both of those included limits are also included in the described subject matter.

Throughout the application, descriptions of various embodiments use "comprising" language. However, it will be understood by one of skill in the art, that in some specific instances, an embodiment can alternatively be described using the language "consisting essentially of" or "consisting of".

For purposes of better understanding the present teachings and in no way limiting the scope of the teachings, unless otherwise indicated, all numbers expressing quantities, percentages or proportions, and other numerical values used in the specification and claims, are to be understood as being modified in all instances by the term "about". Accordingly, unless indicated to the contrary, the numerical parameters set forth in the following specification and attached claims are approximations that may vary depending upon the desired properties sought to be obtained. At the very least, each numerical parameter should at least be construed in light of the number of reported significant digits and by applying ordinary rounding techniques.

The present subject matter relates to a method of inhibiting enzyme activity using an extract of *Boscia senegalen-*

*sis*. In an embodiment, the extract is obtained from leaves of *Boscia senegalensis*. In an embodiment, the extract is obtained using one or more extraction solvents selected from the group consisting of an alcohol, dichloromethane, and hexane. In an embodiment, the one or more extraction solvents is an alcohol. In a further embodiment, the alcohol is ethanol.

In an embodiment, the method includes contacting the extract of *Boscia senegalensis* with one or more enzymes selected from the group consisting of acetylcholinesterase, butyrylcholinesterase, tyrosinase, α-amylase, and glucosidase.

According to an embodiment, a method of preparing an extract of *Boscia senegalensis* can include obtaining one or more *Boscia senegalensis* plant parts, drying the one or more *Boscia senegalensis* plant parts to provide dried plant parts, reducing the dried plant parts to a powder, macerating the powder in a first extraction solvent for a period of time to provide a solution including remaining powder, and filtering the solution. In an embodiment, the remaining powder can be extracted using a second extraction solvent. In an embodiment, the first extraction solvent comprises hexane. In an embodiment, the second extraction solvent includes a mixture of dichloromethane and ethanol. In an embodiment, the powder can be macerated for about three days at room temperature.

The present subject matter can be better understood by referring to the following examples.

EXAMPLES

Example 1

Preparation of Plant Extracts

One kilogram of dried, powdered *Boscia senegalensis* plant materials was extracted separately by maceration in hexane for three days at room temperature using a shaker apparatus and filtered. The residual parts were then extracted again with Dichloromethane (D):Ethanol (E) (1:1, v/v) for 3 days. The filtrate of each extract was evaporated under reduced pressure using a rotatory evaporator. Dry crude hexane and D:E extracts were obtained.

Example 2

Cholinesterase Inhibition Assay

An extract solution including the *Boscia senegalensis* extract (50 µL) and DTNB (5,5-dithio-bis(2-nitrobenzoic) acid) (3 mM 125 µL) was combined with an enzyme solution including acetylcholinesterase (0.265 u/mL AChE) or butyrylcholinesterase (0.026 u/mL BChE) (25 µL) in Tris-HCl buffer (pH 8.0) and added to the substrates [acetylthiocholine iodide (15 mM ATCI) or butyrylthiocholine chloride (1.5 mM BTCI, 25 µL)]. Likewise, a blank sample (prepared in the same manner but without the extract) was prepared and all the absorbances were recorded at 405 nm after 15 minutes of incubation at 25° C. Milligrams of galantamine equivalents per gram of dry extract (GALAEs/g extract) were the measurement unit.

Example 3

Tyrosinase Inhibition Assay

The *Boscia senegalensis* extract solution (25 µL) was added to an enzyme solution including tyrosinase solution (200 u/mL, 40 µL) and phosphate buffer (40 mM, 100 µL, pH 6.8) and the mixture was disposed in a 96-well microplate and then incubated for 15 minutes at 25° C. The reaction was started using L-DOPA (3,4-dihydroxy-L-phenylalanine), (10 mM, 40 µL), then the absorbances were recorded at 492 nm after 10 minutes of incubation at room temperature. Similarly, a blank sample (prepared in the same manner but without the extract) was prepared and analyzed by the same method. Milligrams of kojic acid equivalents per gram of dry extract (KAE/g extract) were the measurement unit.

Example 4

α-Amylase Inhibition Assays

A reaction mixture including the *Boscia senegalensis* extract solution (25 µL) and an enzyme solution including α-amylase solution (10 u/mL, 50 µL) in phosphate buffer (pH 6.9 with 6 mM sodium chloride) was added to a starch solution (50 µL, 0.05%). The reaction was stopped by adding HCl (25 µL, 1 M), after that an iodine-potassium iodide solution was added (100 µL). As well, a blank sample (prepared in the same method but without the extract) was prepared, and all the absorbances were recorded at 630 nm after 10 minutes of incubation at 37° C. Millimoles of acarbose equivalents per gram of dry extract (ACAEs/g extract) were the measurement unit.

Example 5

Glucosidase Inhibition Assay

A reaction mixture including the *Boscia senegalensis* extract solution (*Boscia senegalensis* extract (50 µL) and glutathione (0.5 mg/mL, 50 µL)) and the enzyme solution ((α-glucosidase solution (0.2 u/mL 50 µL) in phosphate buffer (pH 6.8) and PNPG (4-N-trophenyl-a-D-glucopyrano-side), (10 mM, 50 µL)) was stopped after 15 minutes of incubation at 37° C. with sodium carbonate (50 µL, 0.2 M). As well, a blank sample was prepared in the same way but without the extract and all of the absorbances were recorded at 400 nm. Millimoles of a carbose equivalents per gram of dry extract (ACAEs/g extract) were the measurement unit. The results are shown in Table 1 below.

TABLE 1

| Plant | AChE inhibition (mg GALAE/g extract) | | BChE inhibition (mg GALAE/g extract) |
|---|---|---|---|
| Hexane extract | | | |
| *B. sengalensis* (leaves) | 3.85 ± 0.17 | | 0.52 ± 0.03 |
| Dichloromethane/Ethanol (DE) extract | | | |
| *B. sengalensis* (leaves) | NA | | 1.09 ± 0.01 |
| Plant | Tyrosinase inhibition(mg KAE/g extract) | Amylase inhibition (mmol ACAE/g extract) | Glucosidase inhibition (mmol ACAE/g extract) |
| Hexane Extract | | | |
| *B. sengalensis* (leaves) | 109.49 ± 1.87 | 0.64 ± 0.03 | 5.31 ± 0.13 |
| Dichloromethane/Ethanol (DE) extract | | | |
| *B. sengalensis* (leaves) | 113.22 ± 3.19 | 0.58 ± .02 | 6.08 ± 0.01 |

It is to be understood that the present methods are not limited to the specific embodiments described above, but encompass any and all embodiments within the scope of the generic language of the following claims enabled by the embodiments described herein, or otherwise shown in the drawings or described above in terms sufficient to enable one of ordinary skill in the art to make and use the claimed subject matter.

We claim:

1. A method of preventing or inhibiting acetylcholinesterase, butyrylcholinesterase, tyrosinase, α-amylase, and glucosidase activity, comprising:
   providing a hexane extract of *Boscia senegalensis* leaves; and
   contacting the extract of *Boscia senegalensis* leaves with one or more enzymes selected from the group consisting of acetylcholinesterase, butyrylcholinesterase, tyrosinase, α-amylase, and glucosidase.

2. The method of claim 1, wherein the extract of *Boscia senegalensis* leaves is prepared by a method, comprising:
   obtaining *Boscia senegalensis* leaves;
   drying the *Boscia senegalensis* leaves to provide dried plant parts;
   reducing the dried plant parts to a powder;
   macerating the powder in hexane for a period of time to provide a solution including remaining powder; and
   filtering the solution.

3. The method of claim 2, wherein the remaining powder is extracted using a second extraction solvent.

4. The method of claim 2, wherein the powder is macerated for about three days at room temperature.

5. The method of claim 3, wherein the second extraction solvent comprises a mixture of dichloromethane and ethanol.

* * * * *